United States Patent

Andersson

[11] Patent Number: 6,049,280
[45] Date of Patent: Apr. 11, 2000

[54] IDENTITY AND COW ESTRUS INDICATOR

[75] Inventor: Lars Andersson, Ymervägen, Sweden

[73] Assignee: Alfa Laval Agri AB, Tumba, Sweden

[21] Appl. No.: 09/145,767

[22] Filed: Sep. 2, 1998

Related U.S. Application Data

[62] Division of application No. 08/737,885, Nov. 27, 1996, and a division of application No. PCT/SE95/00630, Nov. 27, 1996.

[30] Foreign Application Priority Data

Jun. 1, 1994 [SE] Sweden .................................. 9401890

[51] Int. Cl.$^7$ .................................................. G08B 23/00
[52] U.S. Cl. ..................... 340/573.3; 340/573.4; 340/539; 340/825.36; 600/549; 119/51.02
[58] Field of Search ............................ 340/573.3, 573.1, 340/573.4, 825.36, 539, 572.8, 572.7, 825.72; 600/549; 119/51.02

[56] References Cited

U.S. PATENT DOCUMENTS

| | | |
|---|---|---|
| 3,557,758 | 1/1971 | Lack ..................................... 119/51.02 |
| 4,274,083 | 6/1981 | Tomoeda ............................. 340/825.72 |
| 4,598,275 | 7/1986 | Ross et al. ............................. 340/573.4 |
| 4,798,175 | 1/1989 | Townsend et al. .................. 340/572.7 |
| 4,865,044 | 9/1989 | Wallace et al. .......................... 600/549 |
| 5,497,149 | 3/1996 | Fast ......................................... 340/988 |
| 5,621,388 | 4/1997 | Sherburne et al. .................. 340/573.4 |

*Primary Examiner*—Benjamin C. Lee
*Attorney, Agent, or Firm*—Hovey, Williams, Timmons & Collins

[57] ABSTRACT

A device for transmitting data from a movable unit such from a domestic animal contains a conventional passive transponder unit (1) which is coupled to an antenna (3). The transponder (1) comprises means (23) for storing electrical energy comprised in electrical voltage pulses received on the antenna (3) and can by means of the stored energy transmit on the antenna (3) pulse sequences carrying information such as identification data for the device. Further, in the device a permanent electrical current source such as a lithium battery (9) is provided, which powers a processor (7). The processor (7) receives signals from a motion sensor (15) and is coupled to a transmitter (11) having an antenna (13) and can activate the transmitter (11) for transmitting radio signals having a good range, when the motion detector (15) signals an increased activity, such as for a non-milking cow during the estrus period.

14 Claims, 3 Drawing Sheets

IDENTITY AND COW ESTRUS INDICATOR

This is a divisional application of application Ser. No. 08/737,885, and a divisional of PCT/SE95/00630, filed Nov. 27, 1996 and entitled IDENTITY AND COW ESTRUS DETECTOR.

TECHNICAL FIELD

The present invention relates to a movable device for automatic indication both of identity and of other variables, the device being in particular intended to be carried by a domestic animal such as a cow.

BACKGROUND

Identification systems for domestic animals which comprise a passive transponder unit attached to the animal are well-known, see e.g. the patent U.S. Pat. No. 4,510,495. In such a system, in the transponder unit receiver circuits are provided for receiving radio waves of high frequency and for storing energy drawn from these waves. Further there are transmitter circuits for transmitting, by means of such stored energy and by radio waves, identity information which uniquely identifies the transmitting unit and thereby the domestic animal to which the transponder unit is attached.

In the patent U.S. Pat. No. 4,247,758 for James A. Rodrian it is that a domestic animal such as a dairy cow is provided with a transponder unit which is connected to an electronic counter register powered by a battery for storing the number of signals obtained from a motion detector or sensor. When the transponder is located within a region which is reached by radio signals from a questioning unit, the transponder unit transmits data by means of radio signals data, this data comprising information which constitutes an identification number of the domestic animal and also indicates the number of movements that the domestic animal has made. By evaluating this latter transmitted number it is possible to decide whether the cow is or is not in the estrus period.

In the European patent having the publication No. EP-B1 0 087 015, also for James A. Rodrian, a similar device is disclosed where the transponder unit instead transmits data indicating whether the number of counted movements during a predetermined time period exceeds the reference value by a predetermined amount.

A transponder unit having a motion sensor and a counter for the number of movements is also disclosed in the patent U.S. Pat. No. 4,618,861 for John W. Gettens et al., where the supply of electrical current instead is provided by the way that the motion sensor in the conventional way generates electrical pulses and by storing and utilizing the energy of the pulses for the transmission of information.

In the use of passive transponders having no interior own current supply, at each operation thereof energy must be provided from the outside. It is made, as has been mentioned above, usually by means of high frequency energy transferred by radio waves, the energy being stored in a capacitor in the unit. The stored energy is then used for transmitting a radio signal carrying some type of desired information. For natural reasons such high frequency energy can only be transferred over relatively restricted distances, of the magnitude of order of one or a few meters at most. When an identification system also is used for collecting data, for example for detection of the number of movements or accelerations, some type of an active or more powerful current supply must be arranged, at least for driving a clock and a register, in which the collected data are stored.

Therefore, when such collecting of data is to performed, in most cases a battery is required. A battery has a limited useful lifetime, which is a distinctive disadvantage for identification units, which in the ideal case are to be attached to the animal and are to remain there and be operative for a long time period. In certain cases the motion sensor, see the mentioned patent for John W. Gettens, can itself, having no current supply from the outside, generate the pulses which are used for modifying a register or a memory.

For identification devices which are to transmit their information over long distances, it must be possible to transmit sufficiently strong radio signals and therefor a current supply of the type battery is required. It can be particularly important in the detection of estrus in cows, since they can go loosely during the non-milking period and are seldom collected to some feeding place or similar place. Such a transmission of information over long distances utilizing the energy of a battery should however be executed as seldom as possible, since in at each transmission occasion relatively much energy is consumed.

SUMMARY

It is an object of the invention to provide a data collecting and identification unit which can be used on a domestic animal during a long time without being looked after or without any replacement of components or parts in the unit.

It is a further object of the invention to provide an identification unit for a domestic animal combined with a movement sensor, which can transmit important information also over large distances.

These objects are achieved by the invention, the features and characteristics of which appear from the detailed description and in particular from the appended claims.

Generally thus, in a device for transmitting data from a movable unit such as from a domestic animal a conventional passive transponder unit is arranged which is connected to an antenna. The transponder comprises means for storing electrical energy from electrical voltage pulses received on the antenna and can by means of the stored energy transmit on the antenna pulse sequences carrying information such as identification data of the device. Further in the device, a permanent electrical current source is provided such as a lithium battery, which drives a processor. The processor receives signals from a motion sensor and is coupled to a transmitter having an antenna and can activate the transmitter for transmitting radio signals having a good range, when the motion sensor signals an increased activity, such as for a non-milking cow during the estrus period.

More strictly speaking, in a device for transmitting data from a movable unit, in particular for transmitting identification data and data concerning movement patterns from a domestic animal, a first passive subunit or transponder unit is provided, comprising a receiver antenna and means for storing electrical energy comprised in electrical voltage pulses received on the receiver antenna and further comprising a first transmitter antenna and means for transmitting on the transmitter antenna pulse sequences containing information. In the device also a second sub-device is arranged, comprising an electrical current source of battery type and a second transmitter antenna and means for transmitting pulse sequences containing information on this second transmitter antenna. The second subdevice comprises suitably a processor having memory means for storing data, in particular changing data obtained from a detector or sensor. The processor will signal an abnormal state when the chanting data have changed sufficiently quickly, such as that the data is a counter value indicating the number of detected movements, the processor signalling when the value has increased beyond a predetermined threshold value during a set time, or generally has passed the threshold value in a predetermined direction.

BRIEF DESCRIPTION OF THE DRAWINGS

The invention will now be described in more detail with reference to a non-limiting embodiment and with reference to the accompanying drawings in which.

DETAILED DESCRIPTION

Figure 1:
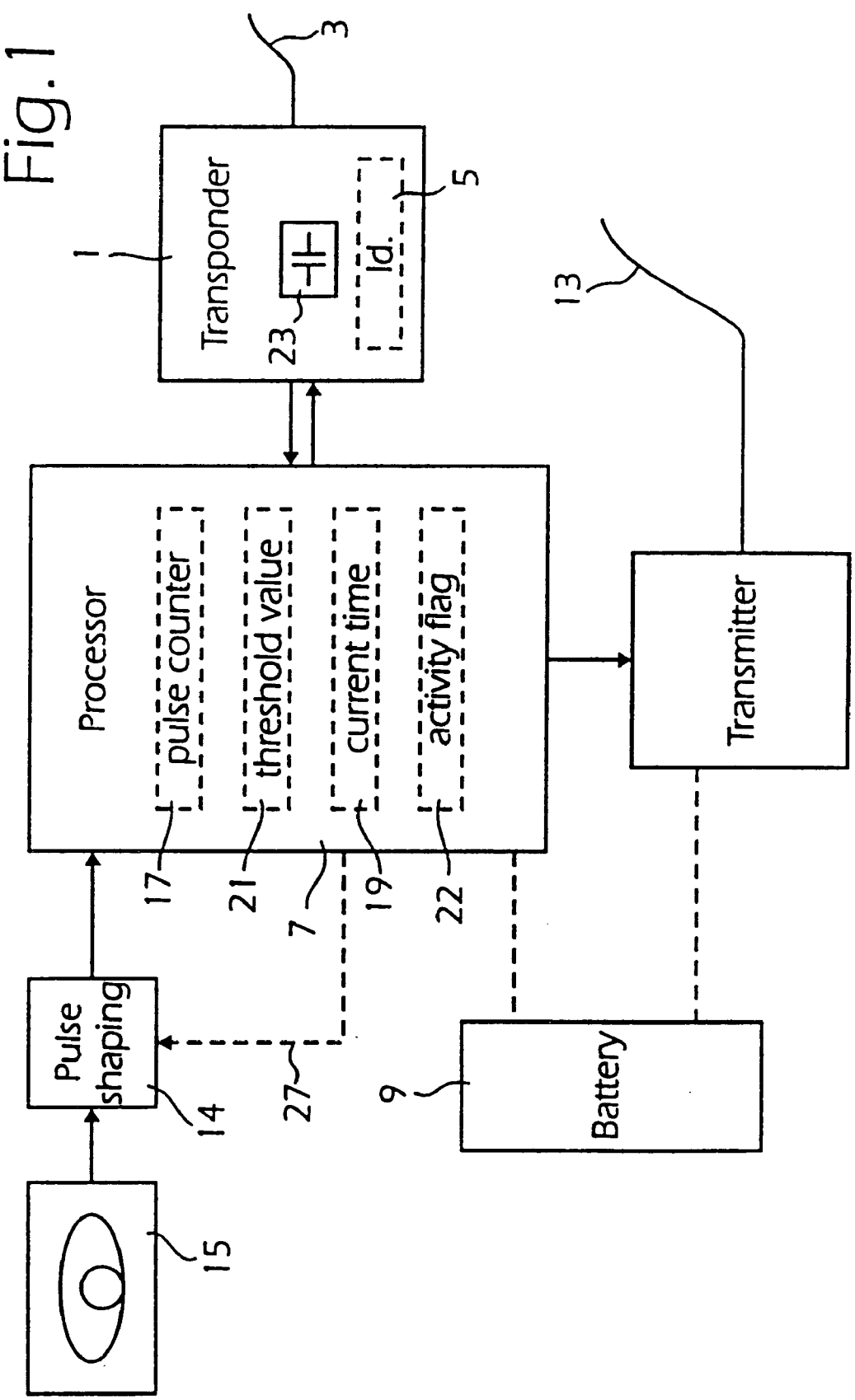
FIG. 1 is a block diagram of circuits for transmitting identification information and of movement data.
Figure 2:
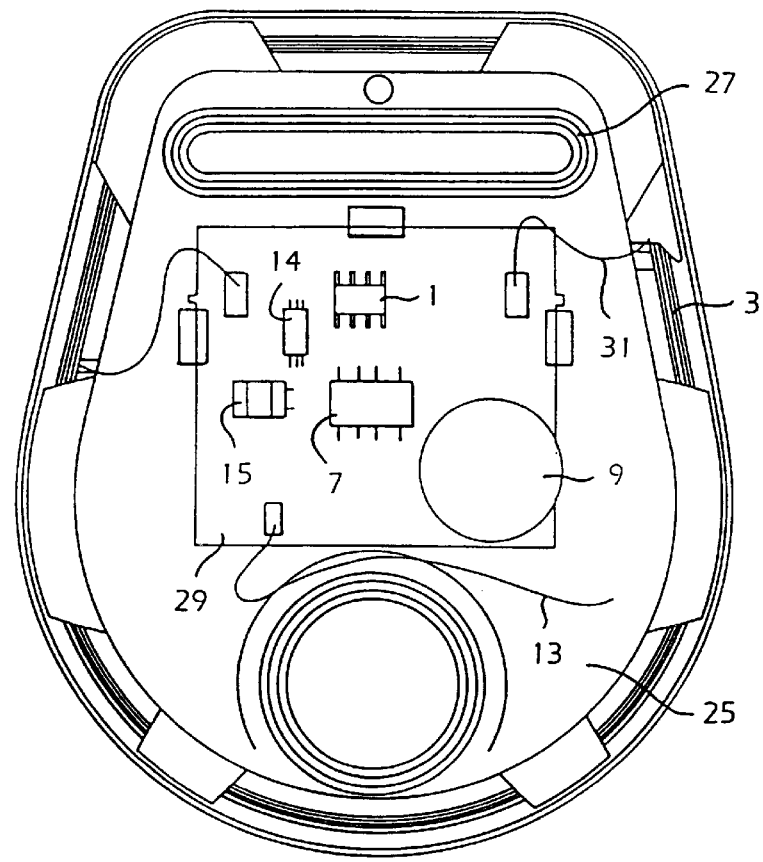
FIG. 2 is a front view of a unit comprising the circuits according to FIG. 1 built into a house.

In FIG. 1, in a block diagram and partly schematically, a device is illustrated intended to be placed in a casing or house, see FIG. 2, which in turn is intended to be for instance suspended around the neck of a domestic animal. The device comprises functions for identification and detection of movements. For the identification a transponder unit 1 is used of principally conventional type, such as a unit which is sold by the company Texas Instruments under the trade name "TIRIS", see also for instance the patent documents DE-C2 3920666, DE-C1 4002801, EP-A1 0480530, EP-A1 0301127, DE-C1 4004196, EP-B1 0299557, U.S. Pat. No. 5,510,495, and U.S. Pat. No. 5,028,918, and it will not be described here in detail. The transponder 1 comprises an antenna 3 and is susceptible of receiving thereon high frequency energy (frequencies of for instance about 100–200 kHz), which is used for driving circuits in the transponder, primarily for transmitting identification data stored in a register, as is illustrated at 5 in FIG. 1.

The completely passive transponder 1, which for the operation thereof does not require any exterior electrical current source, is connected to a processor 7. The processor is designed for normal electronic processor operations and is provided with memories, clock circuits, etc. The processor 7 has an exterior own constant electrical current supply in the shape of a suitable electrochemical battery such as a lithium battery 9. The battery 9 also supplies power to a transmitter 11 of radio frequency waves, for instance having a frequency in the range of about 30 MHz, and is therefor connected to an antenna 13. The processor 7 receives as an input signal electrical pulses on a line from a motion sensor 15, which preferably is of the type, which is described in the patent U.S. Pat. No. 5,183,056 for Björn Dalén et al, assigned to Siemens Elema AB. The electrical pulses from the detector 15 can be shaped to suitable electrical voltage pulses by a pulse forming circuit 14, before they are delivered to the processor. The processor 7 can also receive signals from the transponder unit 1 and can possibly therethrough also transmit data information by means of the antenna 3 connected to the transponder 1.

The device illustrated in FIG. 1 operates in the following way. The motion sensor 11 detects all the time or permanently the movement of for instance a domestic animal, to which the device is attached in some way as being suspended in a neck chain, and electrical signals indicating the movements are sent to the microprocessor 7. The microprocessor 7 is in the preferred case active only during periodically repeated time intervals such as during some minute in each hour but can also possibly be permanently active and the energy supply to the processor 7 is always provided, during the active time periods thereof, from the battery 9. During the activity period the pulses received from the movement sensor 15 are evaluated and counted, the result being stored in a register as a pulse counter 17.

The processor 7 contains, as has been indicated above, also a clock circuit and it is arranged to store the present time in a register illustrated at 19. By means of the values in these registers, i.e. the number of pulses in the pulse counter 17 and the current time in the register 19, the processor 7 evaluates at each instant when it is active, whether the movement activity or intensity, i.e. the number of movements per time unit, is larger than a threshold value stored in a third register 21. If the movement intensity is sufficiently high, the processor 7 activates the transmitter 11, which is also powered by the battery 9, and transmits a message on the antenna, the message containing both identifying information accessed from the memory of the transponder unit 1, and information signalling that the movement intensity now is larger than the threshold value. Further, a flag in a register 22 is set indicating that the movement intensity is now high. By the battery operation of the transmitter 11 the signal issued from the antenna 13 will obtain a reasonably large transmission range, for instance of the magnitude of order of hundreds of metres.

When the whole device instead approaches a specially arranged 4 questioning station, not shown, which for domestic animals can be located at the entrance of a feeding place and which issues pulses of a frequency of the magnitude of order 100–200 kHz, and when the device is sufficiently close to the questioning station, for instance 50 cm at most from the antenna thereof, the electrical energy of the radio waves can be received by the transponder unit 1 by means of its associated antenna 3. The transponder antenna 3 operates in a similar manner as the secondary winding in a transformer, and the received energy or induced energy is stored in a suitable way, for instance in a capacitor, indicated at 23. The energy stored is used by the transponder unit 1 for then transmitting on its antenna 3 identifying information and also a data value accessed from the activity flag in the register 22 in the processor 7 indicating whether the movement intensity at the latest measurement has exceeded or was lower than the threshold value, which is stored in the register 21 in the processor 7.

The radio signals of a higher frequency issued from the antenna 13 are also received by a receiver unit, not shown, for instance the same questioning station which has been already described, and are evaluated in a suitable way as well as the mentioned data value transmitted by the transponder unit 1. When thus a signal of increased movement intensity is received, particular steps can be made for giving an indication to animal keeping persons that now the right time has arrived for executing insemination or similar measures.

Figure 4:
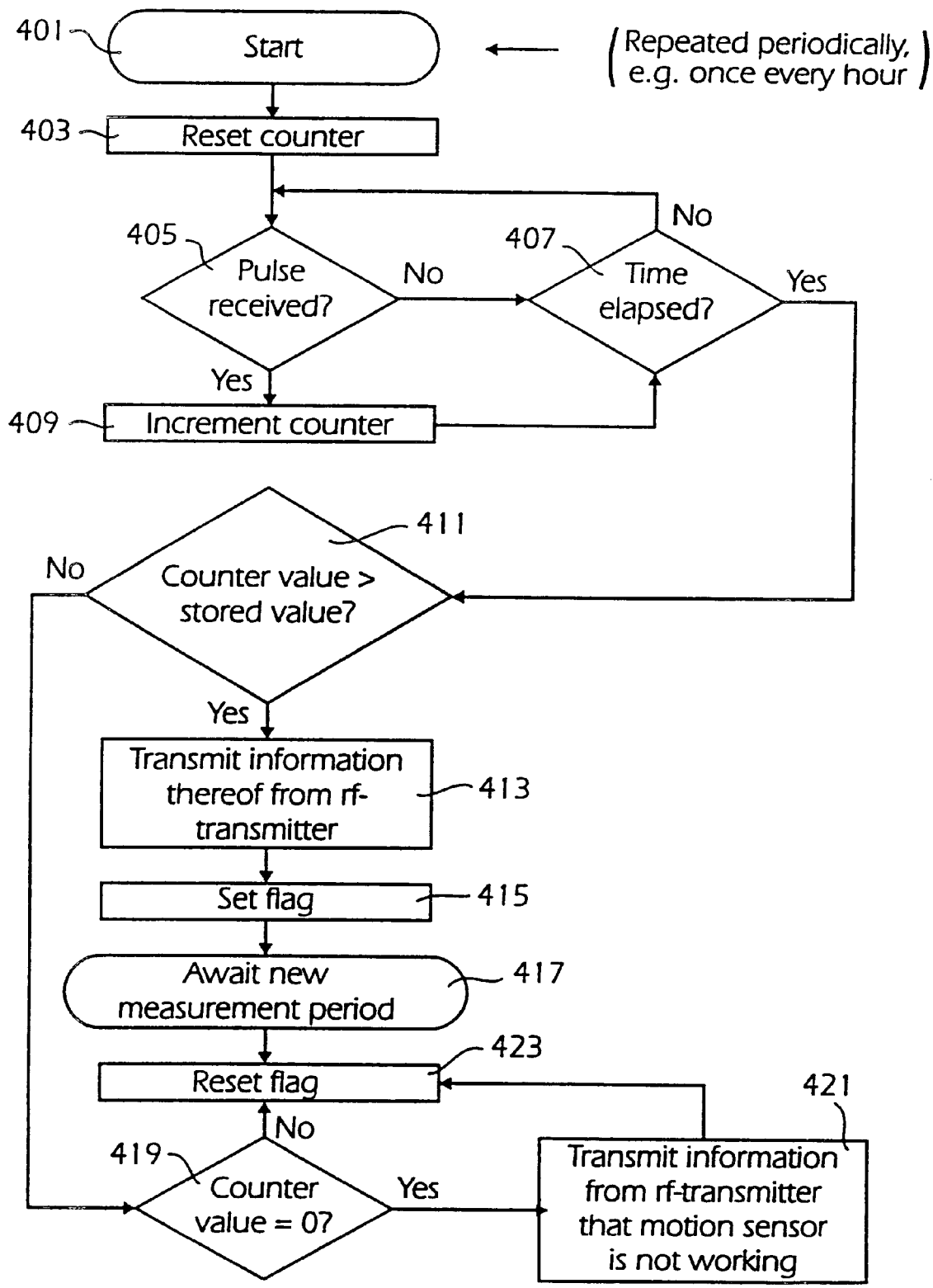

In FIG. 4 an example of a flow diagram is illustrated comprising the various operational steps performed by the processor. First it is thus awaited that the procedure for measuring movement activity is to be started, by activating the processor 7, for instance by some suitable timing circuit, not shown, therein. The procedure then starts in a start block 401, after which the counter 17 is reset to zero in a block 403. Then it is tested in a block 405 whether any pulse has been received from the motion sensor 15. If it is not the case, it is decided in a block 407, whether the time of the activity measurement has elapsed, i.e. for instance that a time period of one minute has elapsed since the procedure was started. If it is not the case, the procedure returns to the block 405 for questioning if any new pulse has arrived.

If it is decided in the block 405 that a new pulse has arrived, the counter 17 is incremented in a block 409, after which the procedure continues to the block 407 for deciding again whether the time of the measurement has elapsed. If it is decided in the block 407 that the time has elapsed, it is determined in a block 411, whether the value of the counter is larger than the threshold value stored in the register 21. If it is true, in a block 413 the transmitter 11 is started for transmitting information that the activity is now high for the animal in question. After that the flag stored in the register 22 is set in a block 415, and then the procedure is ended in a block 417 for awaiting a new measuring period.

If it was decided in the block 411, that the counter value stored in the register 17 in the processor 7 does not exceed the threshold value, the procedure continues to a block 419. Therein it is decided whether any pulses at all has been counted in the procedure, i.e. if the counter in the register 17 still is equal to zero. If it is the case, the movement detector is very probably faulty and then the procedure continues to a block 421, where the rf-transmitter 11 is activated for transmitting information that the motion detector of the domestic animal probably is faulty and needs to be replaced. Then in a block 423 the flag stored in the register 22 is reset, after which the procedure is ended in the block 417. If it was decided in the block 419, that at least one pulse has been counted, it can be assumed, that the movement detector is still operative but that the activity is low, and then the procedure continues to the block 423 for resetting the activity flag, after which the procedure as above is ended in the block 417.

In FIG. 2 the circuits of FIG. 1 are illustrated as built into a casing or house 25, comprising holes or openings 27 for attachment to a neck chain, neck belt or similar device (not shown) of a domestic animal. A circuit board 29 is mounted In the house 25 and comprises the circuits illustrated in FIG. 1 connected by conductive paths, not shown, on the board 25. The antenna 3 is arranged in the shape of a winding having several turns located directly inside the circumference of the house 25 and is through electrically conducting wires 31 connected to electrically conducting areas of the board 25. The antenna 13 for radio frequency comprises a shorter electrical conducting wire also connected to a suitable conducting area on the board 25.

Figure 3:
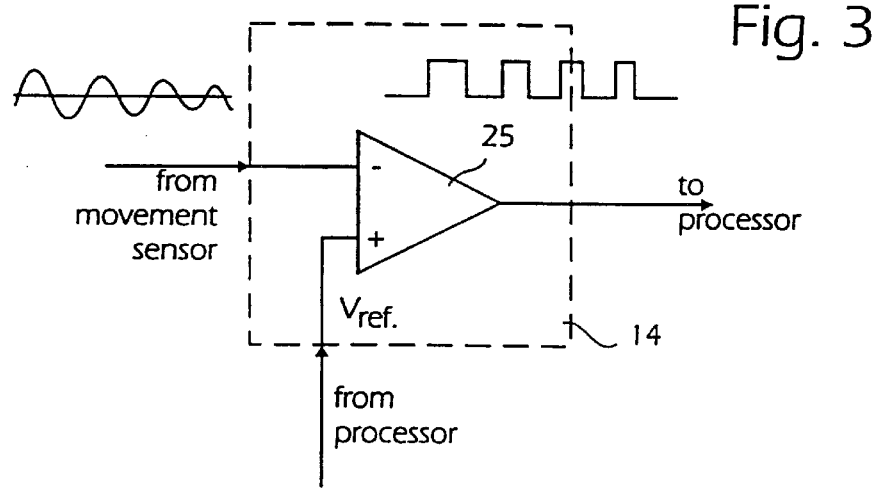
FIG. 3 is a circuit diagram of an embodiment of a pulse forming circuit and FIG. 4 is a flow diagram of a procedure executed by a processor comprised in the circuits of FIG. 1.

A simple embodiment of the pulse shaping circuit 14 is illustrated in FIG. 3. The output signal from the motion detector 15 is supposed to be of type sinus signal having a somewhat varying frequency and a decreasing amplitude for each detected movement. It is provided to an operational amplifier 33 on one of its input terminals, for instance its inverting terminal, a reference voltage Vref. being applied to its other input terminal. The output signal from the operational amplifier will then have a shape comprising pulses of a suitable constant voltage level but having somewhat varying length or width. The pulses are evaluated in a suitable manner by the microprocessor 7, for instance by counting the number thereof. The reference voltage $V_{ref}$ can be controlled by the microprocessor through a DA-converter or similar device, not shown, built into it and thus the non-inverting input terminal of the operational amplifier 25 can be connected to the processor 7 through a line 27, shown in dotted lines in FIG. 1.

In an embodiment of the device according to FIG. 1 the transmitter 11 can alternatively be the transmitter part which is conventionally arranged in passive transponders, and in that case naturally the antenna 13 is the same as the antenna 3 for the transponder unit 1, i.e. the transmitter 11 and the antenna 13 are omitted and the battery 9 delivers, at the particular occasions described, energy for operation of the transponder unit 1.

What is claimed is:

1. A device for transmitting data from a movable unit, in particular for transmission of identification data and data associated with movement patterns of a domestic animal, comprising:
    a first passive subdevice comprising:
        a receiver antenna and means for storing electrical energy comprised in electrical voltage pulses received on the receiver antenna,
        a transmitter antenna and means for transmitting on the transmitter antenna pulse sequences containing said data, and
    a second subdevice comprising:
        an electrical current source for supplying electrical current during a long lime without recharging, and
        a transmitter antenna and means for transmitting, on the transmitter antenna, pulse sequences for containing information said data.

2. A device according to claim 1, the second subdevice including memory means for storing data including at least one of changing data obtained from a detector and a data value indicating the current time.

3. A device according to claim 2, wherein the means in the first subdevice for transmitting pulse sequences containing said data are arranged to transmit identification data and other data in the pulse sequences.

4. A device according to claim 3, wherein the means in the first subdevice for transmitting pulse sequences containing said data is arranged to transmit in the other data in these pulse sequences data obtained from the memory means in the second subdevice.

5. A device according to claim 3, wherein the means in the second subdevice for transmitting pulse sequences containing said data are arranged to transmit identification data and other data in these pulse sequences.

6. A device according to claim 2, wherein the means in the second subdevice for transmitting pulse sequences containing said data is arranged to transmit them when a changing data value stored in its memory means passes in a predetermined direction a threshold value also stored in its memory means.

7. A device according to claim 6, wherein said transmitting means in said second subdevice is arranged to transmit said pulse sequences when said changing data valued stored in the memory means of the second subdevice exceeds said threshold value.

8. A device according to claim 2 further comprising:
    a detector comprised in the second subdevice for detecting an exterior quantity, and
    an evaluating unit for evaluation of signals obtained from the detector and for storing in the memory means the result of this evaluation.

9. A device according to claim 8, wherein said detector in said second subdevice is a motion detector.

10. A device according to claim 2, wherein the means in the first subdevice for transmitting pulse sequences containing said data are arranged to transmit identification information and other data in the pulse sequences.

11. A device according to claim 2, wherein the means in the second subdevice for transmitting pulse sequences containing said data are arranged to transmit identification data and other data in these pulse sequences.

12. A device according to claim 1, wherein the means in the second subdevice for transmitting pulse sequences containing said data are arranged to transmit identification data and other data in these pulse sequences.

13. A device according to claim 12, wherein the means in the first subdevice for transmitting pulse sequences containing said data are arranged to transmit in the other data in these pulse sequences data obtained from the second subdevice.

14. A device according to claim 1, wherein said electrical current source of said second subdevice comprises an electrochemical battery.

* * * * *